(12) United States Patent
Gancet

(10) Patent No.: US 6,673,959 B2
(45) Date of Patent: Jan. 6, 2004

(54) PREPARATION OF CARBOXYLIC ESTERS CATALYZED BY A SULPHONIC ACID

(75) Inventor: Christian Gancet, Lons (FR)

(73) Assignee: Atofina, Puteaux (FR)

( * ) Notice: Subject to any disclaimer, the term of this patent is extended or adjusted under 35 U.S.C. 154(b) by 6 days.

(21) Appl. No.: 09/878,244

(22) Filed: Jun. 12, 2001

(65) Prior Publication Data

US 2002/0026075 A1 Feb. 28, 2002

(30) Foreign Application Priority Data

Jun. 19, 2000 (FR) ............................................. 00 07784

(51) Int. Cl.[7] .................. C07C 69/52; C07C 69/02; B01D 3/34
(52) U.S. Cl. .................. 560/205; 560/224; 560/231; 203/60
(58) Field of Search ................. 560/205, 224, 560/231; 203/60

(56) References Cited

U.S. PATENT DOCUMENTS

| | | | | |
|---|---|---|---|---|
| 4,055,590 A | * | 10/1977 | Gruber et al. | 560/179 |
| 4,329,492 A | * | 5/1982 | Andoh et al. | 560/205 |
| 4,833,267 A | * | 5/1989 | Nakashima et al. | 60/205 |
| 4,868,329 A | * | 9/1989 | Powanda et al. | 560/205 |
| 4,946,029 A | * | 8/1990 | Frank et al. | 203/29 |
| 5,645,696 A | * | 7/1997 | Woo et al. | 203/60 |
| 5,821,383 A | * | 10/1998 | Haussling et al. | 560/205 |
| 6,146,534 A | * | 11/2000 | Grendze et al. | 210/635 |

FOREIGN PATENT DOCUMENTS

| | | |
|---|---|---|
| DE | 40 17 903 | 12/1991 |
| EP | 0 775 687 | 5/1997 |

* cited by examiner

*Primary Examiner*—Alan L. Rotman
*Assistant Examiner*—Taylor V Oh
(74) *Attorney, Agent, or Firm*—Smith, Gambrell & Russell, LLP

(57) ABSTRACT

The preparation of a carboxylic ester by direct reaction of a carboxylic acid and an alcohol catalyzed by a sulphonic acid $R-SO_3H$ is carried out in the presence of a solid comprising tertiary amine functions.

8 Claims, No Drawings

PREPARATION OF CARBOXYLIC ESTERS CATALYZED BY A SULPHONIC ACID

FIELD OF THE INVENTION

The present invention relates to the field of carboxylic esters and its subject is more particularly their synthesis by direct reaction of a carboxylic acid and an alcohol.

BACKGROUND OF THE INVENTION

This reaction is generally catalyzed by an acid which may be sulphuric acid or an acidic resin, but very frequently a sulphonic acid R—$SO_3H$ such as methanesulphonic acid because sulphonic acids make it possible, among other advantages, to obtain carboxylic esters of better quality. However, sulphonic acids, and in particular methanesulphonic acid, have the disadvantage of forming, during the reaction, a small quantity of sulphonic esters of the alcohol which bring about the presence of residual sulphur in the desired carboxylic ester and whose hydrolysis generates the formation of free acidity which is harmful to the quality of the product.

In the case of light carboxylic esters which can be distilled without degradation, the problem may be solved by using a heavy sulphonic acid for which the ester formed may be separated from the carboxylic ester by distillation. However, this solution is not appropriate in the case of degradable carboxylic esters; the reaction product must in this case be treated separately on a resin in order to remove the sulphonic ester formed.

It is known that an irreversible quaternization reaction occurs between a tertiary amine $NR^1R^2R^3$ and an alkyl-donating compound such as a sulphonic ester R—$SO_3$-Alkyl according to the following scheme:

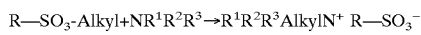

R—$SO_3$-Alkyl+$NR^1R^2R^3$→$R^1R^2R^3AlkylN^+$ R—$SO_3^-$

This reaction has even been used to carry out post-treatments of esters so as to remove therefrom certain sulphonic esters which are present. However, this requires an additional step in the process for the manufacture of the esters and is not therefore easy to carry out.

DESCRIPTION OF THE INVENTION

It has now been found that this quaternization reaction can occur during the reaction for the synthesis of the carboxylic esters itself. Not only is the quaternization reaction possible and makes it possible to remove the sulphonic esters as they are formed, but in addition the presence of the tertiary amine does not at all modify the performance of the sulphonic acid catalyst.

The subject of the invention is therefore a process for the preparation of a carboxylic ester by direct reaction of a carboxylic acid and an alcohol catalyzed by a sulphonic acid R-$SO_3H$, characterized in that the procedure is carried out in the presence of a solid comprising tertiary amine functions in free form.

As solids comprising tertiary amine functions, there may be used in accordance with the present invention organic polymers or copolymers with tertiary amine functions which are well known in the art as anion exchangers. As such, it is possible more particularly to use polystyrene-based resins which are crosslinked in particular with divinylbenzene, acrylic or phenylacrylic resins, acrylic resins which are crosslinked with divinylbenzene, or resins of the phenol-formaldehyde type. These resins carry tertiary amine functional groups which are attached by various techniques known per se, generally after formation of polymers or copolymers. There may also be mentioned the polyvinylpyridines obtained by polymerization of 4-vinylpyridine. Such anion-exchange resins are commercially available under various names such as, for example, Amberlite, Duolite, IRA and Reillex.

The quantity of solid to be used can vary within wide limits. It is generally between 0.01 and 20% relative to the weight of the reaction mixture (acid+alcohol+optional solvent), preferably between 0.1 and 5%.

The process according to the invention may be applied to the preparation of any carboxylic ester whose direct synthesis from the corresponding carboxylic acid and alcohol is catalyzed by a sulphonic acid R—$SO_3H$. It applies in particular to the synthesis of the esters derived from carboxylic acids such as acrylic or methacrylic acids or fatty acids such as heptanoic acid or stearic acid, and mono-, di- or polyfunctional alcohols such as isopropanol, 2-ethylhexanol, diisopropylene glycol, diisobutylene glycol, polyethylene glycols or trimethylolpropane.

As sulphonic acids R-$SO_3H$, there may be mentioned more particularly those in which R is an aliphatic or aromatic radical, such as the acids $CH_3(CH_2)_nSO_3H$ with n ranging from 0 to 3 and p-toluenesulphonic acid. The preferred sulphonic acid is methanesulphonic acid.

The esterification reaction proper is carried out under the usual operating conditions, that is to say:

carboxylic acid/alcohol molar ratio ranging from 1 to 10, preferably of between 1 and 5, temperature of between 50 and 200° C., preferably of between 80 and 150° C., quantity of sulphonic acid R—$SO_3H$ of between 0.1 and 5% relative to the weight of carboxylic acid, preferably of between 0.5 and 2%.

It is possible to carry out the procedure in the absence of solvent or in a mixture with a solvent such as toluene or heptane. The quantity of solvent may vary within wide limits, but it is generally between 5 and 95% relative to the weight of the reaction mixture (acid+alcohol+solvent), preferably between 5 and 50%.

The esterification reaction may be carried out batchwise, semicontinuously or continuously.

At the end of the reaction, the solid may be separated by simple filtration or any other equivalent means.

EXAMPLES

The following examples which illustrate the invention without limiting it relate to the esterification of trimethylolpropane (TMP) with heptanoic acid.

Comparative Example 1

60 g (0.46 mol) of heptanoic acid, 20 g (0.149 mol) of trimethylolpropane and 100 ml of toluene were introduced into a round-bottomed flask placed on a heating bath and equipped with a condenser and a Dean Stark, and then the heating bath was switched on and set at 150° C., the desired temperature.

When the toluene started to reflux in the Dean Stark (at about 120° C.), 1.2 g of anhydrous methanesulphonic acid were injected and, after 90 minutes, the heating bath was removed and the mixture was allowed to cool for about one hour. The mixture was then neutralized with twice a volume of aqueous sodium carbonate solution at 100 g/l corresponding to 10% of the reaction volume, and then washed 4 times with a volume of water corresponding to 10% of the reaction volume, until the aqueous phase was neutralized.

After separation of the phases, the toluene was evaporated off at 65° C. under a vacuum of about 25 mbar, and then the final product was weighed and its analysis was carried out by gas chromatography. The product contained 91.7% by weight of trimethylolpropane triheptanoate (THTMP) and 0.47% by weight of sulphonic ester.

Comparative Example 2

Example 1 was repeated, but by carrying out the procedure with a deficit of heptanoic acid (48 g) and an excess (10 g) of anhydrous methanesulphonic acid.

The final product contained 51.4% by weight of trimethylolpropane triheptanoate (THTMP) and 5.6% by weight of sulphonic ester.

Analysis by gas chromatography and by mass spectrometry showed that the sulphonic ester mainly obtained is the methanesulphonic and diheptanoic ester of trimethylolpropane.

Example 3

Example 1 was repeated, but adding 0.24 g (2.3 mmol) of polyvinylpyridine (PVP Reillex 402), that is 20% by weight relative to the methanesulphonic acid.

The final product contained 92.2% by weight of trimethylolpropane triheptanoate (THTMP) and only 0.11% by weight of sulphonic ester.

Examples 4 to 6

Example 2 was repeated, but adding varying quantities of polyvinylpyridine (PVP Reillex 402), that is 26%, 58% and 100% by weight relative to the methanesulphonic acid.

The results obtained are assembled in the following table.

|  | Example | | | |
|---|---|---|---|---|
|  | 2 | 4 | 5 | 6 |
| PVP (g) | 0 | 2.6 | 5.8 | 10 |
| THTMP (%) | 51.4 | 55.6 | 52.4 | 58.9 |
| Sulphonic ester (%) | 5.6 | 2.6 | 0.22 | 0.1 |

Examples 7 to 10

The esterification conditions are those of Example 1. The resins used are respectively the preceding polyvinylpyridine by way of comparison, Amberlite IRA 96 from Rohm & Haas (styrene-divinylbenzene backbone), Amberlite IRA 92 from Rohm & Haas (macroporous polystyrene backbone) and Duolite A561 from Rohm & Haas (crosslinked phenol-formaldehyde backbone).

The results obtained are assembled in the following table:

| Example | Resin | Mass of resin (g) | Residual sulphur in the final ester (mg/l) |
|---|---|---|---|
| 1 | none | 0 | 250 |
| 7 | Reillex 402 | 0.46 | 112 |
| 8 | IRA 96 | 0.69 | 98 |
| 9 | IRA 92 | 0.79 | 98 |
| 10 | Duolite A561 | 0.42 | 130 |

The resins of Examples 8, 9 and 10, delivered wet and in free amine form, are washed with methanol and dried before use.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. Process comprising preparation of a carboxylic ester by direct reaction of a carboxylic acid and an alcohol catalyzed by a sulphonic acid R—$SO_3H$ in the presence of a solid comprising tertiary amine functions in free form, wherein R has the formula $CH_3(CH_2)_n$, wherein "n" ranges from 0 to 3, further wherein the solid is an organic polymeric or copolymeric anion exchanger, the carboxylic acid being selected from the group consisting of acrylic acid, methacrylic acid, heptanoic acid and stearic acid, and the alcohol being selected from the group consisting of isopropanol, 2-ethylhexanol, diisopropylene glycol, diisobutylene glycol, polyethylene glycols and trimethylolpropane.

2. Process according to claim 1, wherein the solid is a polyvinylpyridine.

3. Process according to claim 1, wherein the solid is a resin of styrene-divinylbenzene, a resin of polystyrene or a resin of phenol-formaldehyde type.

4. Process according to claim 1, wherein the quantity of solid used is between 0.01 and 20% relative to the weight of the reaction mixture.

5. Process according to claim 1, wherein the sulphonic acid is methanesulphonic acid.

6. Process according to claim 4, wherein the quantity of solid is between 0.1 and 5%.

7. Process according to claim 1, wherein the sulphonic acid is p-toluenesulphonic acid.

8. Process according to claim 1, wherein the organic polymer or copolymer anion exchanger is selected from the group consisting of an acrylic resin, a phenylacrylic resin and an acrylic resin crosslinked with divinylbenzene.

* * * * *